(12) United States Patent
Jain et al.

(10) Patent No.: US 9,358,213 B2
(45) Date of Patent: *Jun. 7, 2016

(54) PHARMACEUTICAL COMPOSITIONS OF DULOXETINE

(75) Inventors: Girish Kumar Jain, Delhi (IN); Chandrashekhar Kandi, Hingoli (IN); Vishwanath Nande, Nagpur (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 901 days.

This patent is subject to a terminal disclaimer.

(21) Appl. No.: 12/595,838

(22) PCT Filed: Apr. 19, 2008

(86) PCT No.: PCT/IB2008/051514
§ 371 (c)(1),
(2), (4) Date: Apr. 15, 2010

(87) PCT Pub. No.: WO2008/129501
PCT Pub. Date: Oct. 30, 2008

(65) Prior Publication Data
US 2010/0209498 A1 Aug. 19, 2010

(30) Foreign Application Priority Data

| Apr. 20, 2007 | (IN) | 765/MUM/2007 |
| Apr. 20, 2007 | (IN) | 766/MUM/2007 |
| Apr. 20, 2007 | (IN) | 767/MUM/2007 |
| Apr. 20, 2007 | (IN) | 772/MUM/2007 |
| Apr. 20, 2007 | (IN) | 773/MUM/2007 |
| Apr. 20, 2007 | (IN) | 775/MUM/2007 |
| Apr. 20, 2007 | (IN) | 776/MUM/2007 |

(51) Int. Cl.

| A61K 9/22 | (2006.01) |
| A61K 9/28 | (2006.01) |
| A61K 9/48 | (2006.01) |
| A61K 31/381 | (2006.01) |
| A61K 47/48 | (2006.01) |
| A61K 9/20 | (2006.01) |
| A61K 9/50 | (2006.01) |

(52) U.S. Cl.
CPC ............ *A61K 9/2886* (2013.01); *A61K 9/4808* (2013.01); *A61K 9/4891* (2013.01); *A61K 9/5073* (2013.01); *A61K 9/5078* (2013.01); *A61K 31/381* (2013.01); *A61K 47/48184* (2013.01); *A61K 9/2027* (2013.01); *A61K 9/2059* (2013.01); *A61K 9/2846* (2013.01); *A61K 9/2866* (2013.01); *A61K 9/5026* (2013.01); *A61K 9/5047* (2013.01)

(58) Field of Classification Search
CPC ..... A61K 9/20; A61K 9/2004; A61K 9/2086; A61K 9/28
USPC ................................... 424/464–489
See application file for complete search history.

(56) References Cited

U.S. PATENT DOCUMENTS

| 5,508,276 A | 4/1996 | Anderson et al. | |
| 6,210,716 B1* | 4/2001 | Chen | A61K 9/2081 424/489 |
| 8,758,779 B2* | 6/2014 | Mate | A61K 9/0095 400/474 |
| 2004/0034101 A1* | 2/2004 | Rao | A61K 31/00 514/619 |
| 2004/0121010 A1* | 6/2004 | Hirsh | A61K 9/2054 424/468 |
| 2005/0059654 A1* | 3/2005 | Arneric | A61K 31/135 514/220 |
| 2005/0147663 A1* | 7/2005 | Mohan | A61K 9/2886 424/451 |
| 2005/0250838 A1* | 11/2005 | Challapalli | A61K 9/2031 514/419 |
| 2006/0165776 A1* | 7/2006 | Sesha | A61K 9/4808 424/451 |
| 2006/0193914 A1* | 8/2006 | Ashworth et al. | 424/469 |
| 2006/0198815 A1* | 9/2006 | Barker et al. | 424/78.27 |
| 2007/0141150 A1* | 6/2007 | Kandarapu et al. | 424/472 |
| 2007/0215511 A1* | 9/2007 | Mehta | A61K 9/0056 206/531 |

OTHER PUBLICATIONS

Ning Ma et al (Determination of duloxetine in human plasma via LC/MS and subsequent application to a pharmacokinetic study in healthy Chinese volunteers; Clinica Chimica Acta 380 Jan. 2007 100-105).*
Ma et al: "Dtermination of buloxetine in Human Plasma via LC/MS and subsequent Healthy Chinese Volunteer". Clinica Chimica Acta, Elsevier BV, Amstradm, NL vol. 380, No. 1-2., Mar. 31, 2007.

* cited by examiner

*Primary Examiner* — Micah-Paul Young
(74) *Attorney, Agent, or Firm* — Bio Intellectual Property Srervices LLC (Bio IPS); O. (Sam) Zaghmout

(57) ABSTRACT

The present invention relates to pharmaceutical compositions of duloxetine or pharmaceutically acceptable salts thereof, and processes for their preparation.

6 Claims, No Drawings

PHARMACEUTICAL COMPOSITIONS OF DULOXETINE

FIELD OF THE INVENTION

The present invention relates to pharmaceutical compositions of duloxetine or pharmaceutically acceptable salts thereof, and processes for their preparation.

BACKGROUND OF THE INVENTION

Duloxetine is a selective serotonin and norepinephrine reuptake inhibitor (SSNRI) for oral administration. Eli Lilly markets duloxetine in the United States under the trade name Cymbalta® as a delayed release capsule containing enteric-coated pellets of the duloxetine. It is indicated for the treatment of major depressive disorder and for the treatment of diabetic peripheral neuropathic pain. These enteric-coated pellets are designed to prevent degradation of the drug in the acidic environment of the stomach.

Duloxetine is acid labile and acid hydrolysis of its ether linkage results in a thienyl alcohol and 1-naphthol. 50% of the dosage is hydrolyzed to 1-naphthol within one hour at a pH of 1.0, which is achieved under fasting conditions. At a pH of 2.0, 10% of the dosage degrades to 1-naphthol in one hour and at a pH of 4.0, 10% degradation would take up to 63 hours. Typically, such acid sensitive compounds are formulated as enteric-coated pellets to protect them from degradation.

The enteric dosage forms have been employed to protect the duloxetine from degradation because it is very important that duloxetine should not be exposed to gastric acid prior to absorption. Although it is stable at alkaline pH, it gets destroyed rapidly as pH falls. Therefore, if the micro encapsulation or the enteric coating is disrupted (e.g., by trituration of the compound or chewing the capsule), the duloxetine would be exposed to degradation by the gastric acid in the stomach. Duloxetine was also found to react with many enteric coatings to form a slowly- or even insoluble coating.

U.S. Pat. No. 5,508,276 discloses duloxetine in the form of enteric pellets. The enteric pellet includes a core containing duloxetine and an enteric layer which includes hydroxypropylmethylcellulose acetate succinate.

US Application No. 20060165776 discloses a composition containing a core consisting of duloxetine or its derivatives, the core includes pharmaceutically inert nuclei and duloxetine or its derivatives compressed together, an intermediate and an enteric layer, wherein the composition is free of alkaline reacting compounds.

US Application No. 20070004795 discloses compositions of duloxetine with buffering agents.

US Application No. 20060079569 discloses oral liquid compositions of duloxetine or its derivatives thereof.

US Application No. 20070292511 discloses delayed release compositions of duloxetine or salts thereof with enteric layer which includes methacrylic acid copolymer and hydroxypropyl methylcellulose phthalate.

The present invention addresses and overcomes the above commonly encountered degradation problems with the formulations of duloxetine.

SUMMARY OF THE INVENTION

In one general aspect there is provided a capsule composition comprising duloxetine or a salt thereof, wherein the capsule is coated with one or more pharmaceutically acceptable enteric polymers. The duloxetine or a salt thereof may be present in the form of powder, granules, pellets, beads, minitablets or microtablets.

Embodiments of the composition may include one or more of the following features. The composition may further include one or more pharmaceutically acceptable excipients selected from the group of fillers, binders, lubricants, glidants, disintegrants, and the like.

In another general aspect there is provided a process for the preparation of the capsule composition of duloxetine or salts thereof. The process includes filling duloxetine or salts thereof in a capsule and coating the capsule with one or more pharmaceutically acceptable enteric coating polymers.

In another general aspect there is provided a melt granulated pharmaceutical composition of duloxetine or salts thereof. The pharmaceutical composition includes duloxetine or salts thereof which may be melt granulated with one or more pharmaceutically acceptable carriers.

Embodiments of the composition may include one or more of the following features. The composition may further include one or more pharmaceutically acceptable excipients selected from the group of fillers, binders, lubricants, glidants, disintegrants, and the like.

In another general aspect there is provided a process for the preparation of melt granulated pharmaceutical composition of duloxetine or salts thereof. The process includes mixing duloxetine or salts thereof with one or more pharmaceutically acceptable carriers to form a mixture and granulating the mixture by melting, mixing, and congealing, optionally with one or more pharmaceutically acceptable excipients.

In another general aspect there is provided a pharmaceutical composition that includes duloxetine or a salt thereof conjugated to ion exchange resin particles.

Embodiments of the composition may include one or more of the following features. The composition may further include one or more pharmaceutically acceptable excipients selected from the group of fillers, binders, lubricants, glidants, disintegrants, and the like.

In another general aspect there is provided a process for the preparation of a pharmaceutical composition of duloxetine or a salt thereof conjugated to ion exchange resin particles. The process includes slurrying anionic exchange resin particles in a solution containing duloxetine; washing the duloxetine resin conjugate; and drying the duloxetine resin conjugate.

In another general aspect there is provided a pharmaceutical composition comprising coated beads of duloxetine or a salt thereof optionally with a stabilizer, wherein the beads of duloxetine or a salt thereof are coated with one or more pharmaceutically acceptable enteric polymers, wherein the enteric polymer is not hydroxypropylmethylcellulose acetate succinate.

The coated beads of duloxetine or a salt thereof may be present in an uncompressed form. The coated beads of duloxetine or a salt thereof are as such not subjected to compression by any suitable means.

Embodiments of the composition may include one or more of the following features. The composition may further include one or more pharmaceutically acceptable excipients selected from the group of fillers, binders, lubricants, glidants, disintegrants, and the like.

The pharmaceutical composition of the invention can be present in the form of pellets, beads, spheroids, a tablet, a minitablet, a microtablet, a capsule, pellets in a capsule, minitablets in a capsule, or combinations thereof.

In another general aspect there is provided a tablet in a tablet composition of duloxetine or salts thereof. The composition includes an inner tablet comprising duloxetine or salts thereof and an outer tablet comprising inert pharmaceutically acceptable excipients.

In another general aspect there is provided a process for making tablet in a tablet composition of duloxetine or a salt thereof. The process includes mixing duloxetine or salts thereof with pharmaceutically acceptable excipients to form a mixture; granulating the mixture with other pharmaceutically acceptable excipients; compressing the granules into tablets; and compressing the tablet with other pharmaceutically acceptable excipients.

Embodiments of the composition may include one or more of the following features. The composition may further include one or more pharmaceutically acceptable excipients selected from the group of fillers, binders, lubricants, glidants, disintegrants, and the like.

In another general aspect there is provided a pharmaceutical composition comprising minitablets of duloxetine or salts thereof along with pharmaceutically acceptable excipients, wherein the duloxetine or salts thereof is not in the form of beads or pellets. The minitablets may further be coated with one or more pharmaceutically acceptable seal coat polymers or enteric polymers.

Embodiments of the composition may include one or more of the following features. The composition may further include one or more pharmaceutically acceptable excipients selected from the group of fillers, binders, lubricants, glidants, disintegrants, and the like.

The details of one or more embodiments of the inventions are set forth in the description below. Other features, objects and advantages of the inventions will be apparent from the description and claims.

DETAILED DESCRIPTION OF THE INVENTION

The inventors have now discovered that duloxetine can be stabilized against acid degradation without reacting with enteric coatings. The enteric coating is insoluble in acid environment, such as stomach, and releases duloxetine in basic environment, such as small intestine. This prevents duloxetine from degradation and provides a stable formulation. Thus, there are provided compatible and stable formulations of duloxetine or salts thereof.

In one of the embodiments, a stable formulation of duloxetine may be prepared by encapsulating duloxetine or a salt thereof in a capsule and coating the capsule with an enteric coat polymer. Thus, the duloxetine does not react with the enteric polymer and the enteric coating further prevents the duloxetine from degradation and provides a stable formulation.

In another embodiment, a stable formulation of duloxetine may be prepared by melt granulating the duloxetine or a salt thereof with a pharmaceutically acceptable carrier. The granules may be further coated with a seal coat polymer and enteric coat polymers. The carrier coats the duloxetine or a salt thereof and hence prevents the exposure of duloxetine or a salt thereof to the enteric polymer and thus provides a stable formulation.

The inventors also have discovered that duloxetine can be stabilized against acid degradation by conjugating it with ion exchange resins. The conjugation between duloxetine and the ion exchange resin particles results from ionic bonds between oppositely charged species because of their mutual electrostatic attraction. The resulting stabilization is sufficient to prevent degradation of duloxetine in acidic pH. It was also discovered that when minitablets of duloxetine or a salt thereof are coated with an enteric polymer and either filled in a capsule or further converted into a tablet composition, it results in stable formulations of duloxetine or salts thereof.

In yet another embodiment, a stable formulation of duloxetine may be prepared by coating beads of duloxetine with an enteric polymer other than hydroxypropylmethylcellulose acetate succinate. The addition of a stabilizer may further provide stability to the formulation and prevent degradation of the duloxetine. The stabilizer neutralizes the acidic groups in the composition and surrounding media thereby maintaining an alkaline pH around the duloxetine particles.

The term "stabilizer" as used herein refers to one or more pharmaceutically acceptable substances capable of preventing degradation of duloxetine by imparting an alkaline pH. The stabilizer creates an alkaline pH around the particles of duloxetine or a salt thereof when water is adsorbed thereon or when water is added. The stabilizer may be present from about 0% to about 90% by weight of the total composition. The pH may be determined by taking a unit dosage of the composition containing for example, 20 mg of duloxetine and dispersing or dissolving the composition in 10 to 100 ml of water.

The stabilizer may be selected from one or more of salts of organic acid or base and salts of an inorganic acid or base and inorganic or organic bases. Suitable salts of inorganic acids include alkali metal salts or alkaline earth metal salts and include calcium carbonate, magnesium carbonate, potassium carbonate, sodium bicarbonate, potassium hydrogen carbonate, anhydrous sodium, potassium or calcium dibasic phosphate, trisodium phosphate, magnesium oxide, and the like. The organic base may be one or more of amino acids like glycine, alanine, asparginine, cysteine, glutamine, leucine, isoleucine, proline, phenylalanine, and the like. The salts of organic acid include sodium citrate, sodium acetate, sodium tartrate and the like. Examples of other stabilizers which may be used include glucosamine, meglumine, tromethamine, ammonia, and the like.

In another embodiment, a pharmaceutical composition of duloxetine or salts thereof may be prepared by mixing duloxetine or a salt thereof with one or more pharmaceutically acceptable excipients and granulating the premix with a binder solution, drying the granules and mixing with other pharmaceutically acceptable excipients. The dried granules may be either lubricated and compressed into minitablets or sized into beads or pellets by extrusion-spheronization. The granules of duloxetine or minitablets of duloxetine or beads/pellets of duloxetine may be further filled into hard gelatin capsules, which may be coated with enteric polymers.

In still another embodiment, a pharmaceutical composition of duloxetine or salts thereof may be prepared by mixing and heating duloxetine and a part of pharmaceutically acceptable carrier along with fluidization. This mix may be then mixed with the remaining part of pharmaceutically acceptable carrier and heated. The pharmaceutically acceptable carrier melts and granulates the duloxetine or salts thereof. The mixture may be cooled and aggregates may be sized into granules. The granules may be mixed with other pharmaceutically acceptable excipients, and may further be coated with seal coat polymers or enteric polymers.

Suitable pharmaceutically acceptable carriers may include one or more of fatty esters, fatty acids and salts thereof, fatty alcohols, fatty amines, fatty amides, glycerides, glycolipids, steroids, natural and synthetic waxes, polyethylene glycol (PEG) or derivatives, and the like.

Polyethylene glycol or its derivatives may include PEG 200, PEG 300, PEG 400, PEG 600, PEG 1000, PEG 4000, PEG 6000, PEG 8000, PEG 20000, polyglycolyzed glycerides, polyethylene glycol-polyoxyethylenes, polyethylene glycol polypropylenes, and polyethylene glycol-polyoxypropylenes.

In still another embodiment, a pharmaceutical composition of duloxetine or salts thereof may be prepared by slurrying duloxetine or a salt thereof in a solution of anion exchange resin particles thereby creating a duloxetine resin conjugate. The duloxetine resin conjugate may be washed, dried and sized to a desirable particle size, which may be then coated with enteric polymers.

The term duloxetine-resin conjugate as used herein refers to a complexation between duloxetine and the ion exchange resin particles resulting from ionic bonds between oppositely charged species because of their mutual electrostatic attraction.

Suitable ion-exchange resin particles may include anionic exchange resin particles which are commercially available as Duolite® resins, Purolite® resins, Amberlite® resins which are cholestyramines, a synthetic anionic exchange polymer in which quaternary ammonium groups are attached to a polystyrene-divinylbenzene co-polymer. The resins may be sized to achieve a desired particle size.

The duloxetine resin conjugate may contain duloxetine in an amount of from about 1% to about 70% by weight and ion exchange resin from about 30% to about 99% by weight.

The duloxetine-resin conjugate may be prepared by slurrying anionic exchange resin particles in a solution containing duloxetine, washing the duloxetine resin conjugate, and drying the duloxetine resin conjugate. The duloxetine resin conjugate may be sized to obtain a complex of the desired size.

The duloxetine resin conjugate may be optionally coated with pharmaceutically acceptable seal coat polymers followed by enteric coating polymers.

In still another embodiment, a pharmaceutical composition of duloxetine or salts thereof may be prepared by layering duloxetine or a salt thereof on inactive core along with a stabilizer and other pharmaceutically acceptable excipients, and coating the beads of duloxetine or a salt thereof thus obtained with seal coat polymers followed by enteric coating with enteric polymers.

The coated beads of duloxetine or a salt thereof may also be prepared by spraying inactive cores with a slurry or a solution of duloxetine or a salt thereof optionally along with other pharmaceutically acceptable excipients and optionally coating the beads of duloxetine or a salt thereof thus obtained with pharmaceutically acceptable seal coat polymers followed by enteric coating with pharmaceutically acceptable enteric polymers.

Alternatively, the coated beads of duloxetine or a salt thereof may also be prepared by a process of extrusion-spheronization or marumerization and optionally coating the beads of duloxetine or a salt thereof thus obtained with pharmaceutically acceptable seal coat polymers followed by enteric coating with pharmaceutically acceptable enteric polymers.

Further, the coated beads of duloxetine or a salt thereof may also be prepared by adsorbing duloxetine or a salt thereof on pharmaceutically acceptable adsorbent, processing the adsorbate into beads of duloxetine or a salt thereof and optionally coating the beads of duloxetine or a salt thereof thus obtained with pharmaceutically acceptable seal coat polymers followed by enteric coating with pharmaceutically acceptable enteric polymers.

Spraying or adsorption can be carried out by a fluidized bed processor, glatt, spray dryer or by any other suitable coating techniques known in the art.

The inactive cores can be made up of one or more of saccharides or derivatives thereof such as polysaccharides, sugars such as mannitol, sorbitol, lactose, sucrose, maltodextrin, starches such as maize starch, rice starch, celluloses such as microcrystalline cellulose, sodium carboxymethyl cellulose, vegetable gums, waxes, and the like.

The adsorbate of duloxetine or a salt thereof can be processed into beads of duloxetine or a salt thereof by extrusion—spheronization or marumerization or any other suitable technique known in the art.

The pharmaceutically acceptable adsorbents may be one or more of colloidal silicon dioxide, calcium silicate, magnesium aluminum silicate, porous ceramics, polypropylene foams, cellulose, cellulose derivatives, polyols, starches, pregelatinized starches, starch derivatives, modified starches, dextrins, maltodextrins, polydextroses, dextroses, calcium carbonate, calcium phosphate, or calcium sulfate.

The slurry or solution of duloxetine or a salt thereof includes duloxetine or a salt thereof suspended or dissolved in water along with one or more polymers such as hydroxypropyl methylcellulose, hydroxypropyl cellulose, polyvinyl pyrrolidone, methacrylates and the like, and optionally with other pharmaceutically acceptable excipients. The slurry of duloxetine or a salt thereof may be milled through a machine adapted for grinding suspensions in order to reduce the particle size of duloxetine.

In still another embodiment, a pharmaceutical composition of duloxetine or a salt thereof may be prepared by mixing duloxetine or a salt thereof with one or more pharmaceutically acceptable excipients and granulating the premix with a binder solution, drying the granules, lubricating the granules and compressing the lubricated granules into minitablets. The minitablets may further be coated with seal coat polymers optionally with polyethylene glycol followed by enteric coating the seal coated minitablets with enteric coat polymers.

The coated minitablets of duloxetine or a salt thereof can be prepared by mixing duloxetine or a salt thereof with other pharmaceutically acceptable excipients to form a premix, optionally converting the premix into granules by dry granulation or wet granulation and compressing the premix or granules into minitablets. The minitablets thus obtained may be further optionally coated with pharmaceutically acceptable seal coat polymers followed by coating with pharmaceutically acceptable enteric polymers.

Alternatively, the coated minitablets of duloxetine or a salt thereof can also be prepared by spraying or adsorbing the slurry or solution of duloxetine or a salt thereof on the inert core minitablets which can be further optionally coated with pharmaceutically acceptable seal coat polymers followed by coating with pharmaceutically acceptable enteric polymers.

The inert core minitablets can be prepared by mixing inert pharmaceutically acceptable excipients, optionally converting the premix into granules by dry granulation or wet granulation and compressing the premix or granules into minitablets.

The slurry or solution of duloxetine or a salt thereof includes duloxetine or a salt thereof suspended or dissolved in water along with one or more polymers such as hydroxypropyl methylcellulose, hydroxypropyl cellulose, polyvinyl pyrrolidone, methacrylates, and the like. The slurry may be milled through a machine adapted for grinding suspensions in order to reduce the particle size of duloxetine.

The minitablets of duloxetine may be present in the form of inlayed or pillowed tablet in a tablet composition of duloxetine or salts thereof, wherein the inner tablet is of duloxetine or salts thereof compressed with an outer tablet of inert excipients.

The pharmaceutically acceptable seal coat polymers may be selected from a group that includes hydroxypropyl methylcellulose, hydroxypropyl cellulose, hydroxyethyl cellulose, hydroxypropyl ethylcellulose, methylcellulose, ethyl cellulose, carboxymethyl cellulose, sodium carboxymethyl cellulose, hydroxyethyl methylcellulose, and mixtures thereof.

The pharmaceutically acceptable enteric coating polymers for coating the capsule are polymers which are insoluble in acidic environment and do not release duloxetine or salt there of for at least 2 hours. Suitable pharmaceutically acceptable enteric coating polymers include one or more of polymerized gelatin, shellac, methacrylic acid copolymer type C NF, cellulose butyrate phthalate, cellulose hydrogen phthalate, cellulose propionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, and acrylic acid polymers and copolymers like methyl acrylate, ethyl acrylate, methyl methacrylate and/or ethyl methacrylate with copolymers of acrylic and methacrylic acid esters such as Eudragit® NE, RL, RS, and the like.

The other pharmaceutically acceptable excipients as used herein include binders, fillers, lubricants, disintegrants, glidants, and the like.

Suitable binders include one or more of povidone, starch, stearic acid, gums, hydroxypropylmethyl cellulose, and the like.

Suitable fillers include one or more of microcrystalline cellulose, lactose, mannitol, calcium phosphate, calcium sulfate, kaolin, dry starch, powdered sugar, and the like.

Suitable lubricants include one or more of magnesium stearate, zinc stearate, calcium stearate, stearic acid, sodium stearyl fumarate, hydrogenated vegetable oil, and the like.

Suitable glidants include one or more of colloidal silicon dioxide, talc or cornstarch, and the like.

Suitable disintegrants include one or more of starch, croscarmellose sodium, crospovidone, sodium starch glycolate, and the like.

The present invention is further illustrated by the following examples which are provided merely to be exemplary of the invention and do not limit the scope of the invention. Certain modifications and equivalents will be apparent to those skilled in the art and are intended to be included within the scope of the present invention.

Example 1

TABLE 1

| No | Ingredients | % w/w |
|---|---|---|
|  | Enteric coated beads of Duloxetine hydrochloride |  |
|  | Inactive core |  |
| 1 | Sugar spheres | 10-90 |
|  | Drug layering |  |
| 2 | Duloxetine hydrochloride | 10-80 |
| 3 | Magnesium oxide | 0.1-10 |
| 4 | Hypromellose | 5-90 |
| 5 | Polyethylene glycol 6000 | 0.5-10 |
| 6 | Talc | 0.5-10 |
| 7 | Purified water | q.s. |
|  | Seal coating |  |
| 8 | Seal coat composition: (Sucrose, Hypromellose, Polyethylene glycol 6000, Purified water) | 1-30 |

TABLE 1-continued

| No | Ingredients | % w/w |
|---|---|---|
|  | Enteric coated beads of Duloxetine hydrochloride |  |
|  | Enteric coating |  |
| 9 | Methacrylic acid copolymer suspension (Methacrylic acid copolymer, sodium hydroxide, Talc, triethyl citrate, purified water) | 5-25 |
|  | Encapsulation |  |
|  | Hard gelatin capsules |  |

Procedure: Hypromellose solution was prepared in water and duloxetine hydrochloride along with PEG 6000 was added to hypromellose solution. Talc and magnesium oxide were dispersed in the above solution using a stirrer. The slurry thus obtained was sprayed on inactive sugar sphere cores in a fluidized bed processor by Wurster technique. The duloxetine beads thus obtained were seal coated by spraying hypromellose, sucrose and polyethylene glycol 6000 solution in water. The seal coated beads were further coated with enteric polymer suspension prepared by mixing methacrylic acid polymer, sodium hydroxide, talc, triethyl citrate in water. The enteric-coated beads of duloxetine hydrochloride were encapsulated in hard gelatin capsules of a suitable size.

Example 2

TABLE 2

| No | Ingredients | % w/w |
|---|---|---|
| 1 | Duloxetine hydrochloride | 10-80 |
| 2 | Lactose | 10-90 |
| 3 | Starch | 10-90 |
| 4 | Povidone | 1-15 |
| 5 | Isopropyl alcohol | q.s. |
| 6 | Purified water | q.s. |
| 7 | Talc | 0.5-10 |
| 8 | Magnesium stearate | 0.5-5 |
| 9 | Colloidal silicon dioxide | 0.5-5 |
|  | Encapsulation |  |
|  | Hard gelatin capsules |  |
|  | Enteric coating of hard gelatin capsules |  |
| 10 | Methacrylic acid copolymer suspension (Methacrylic acid copolymer, sodium hydroxide, Talc, triethyl citrate, purified water) | 5-25 |

Procedure: Duloxetine hydrochloride was mixed with lactose, starch and granulated with povidone solution in isopropyl alcohol-water mixture. The granules were dried and mixed with colloidal silicon dioxide. The granules were either lubricated with magnesium stearate and the lubricated granules were compressed into minitablets of a suitable size using a suitable tooling or sized into beads or pellets by extrusion-spheronization.

The granules as such or minitablets or pellets/beads of duloxetine or a salt thereof were filled into hard gelatin capsules which were further coated with an enteric polymer suspension prepared by mixing methacrylic acid polymer, sodium hydroxide, talc, triethyl citrate in water.

Example 3

TABLE 3

| No | Ingredients | % w/w |
|---|---|---|
| 1 | Duloxetine hydrochloride | 10-80 |
| 2 | PEG 6000 | 0.5-30 |
| 3 | Microcrystalline cellulose | 10-90 |
| 5 | Starch | 10-90 |
| 7 | Talc | 0.5-10 |
| 8 | Magnesium stearate | 0.5-5 |
|   | Seal coating |   |
| 9 | Seal coat composition: (Sucrose, Hypromellose, Polyethylene glycol 6000, Purified water) | 1-30 |
|   | Enteric coating |   |
| 10 | Methacrylic acid copolymer suspension (Methacrylic acid copolymer, sodium hydroxide, Talc, triethyl citrate, purified water) | 5-25 |
|   | Encapsulation |   |
|   | Hard gelatin capsules |   |

Procedure: Duloxetine hydrochloride and a part of polyethylene glycol were mixed together and heated in a fluidized bed, where PEG melted and coated the duloxetine hydrochloride. This mix was then mixed with the remaining part of polyethylene glycol, heated, where PEG melted and granulated the duloxetine hydrochloride. The molten mass of duloxetine hydrochloride and PEG 6000 was cooled to room temperature and sized into granules using a multimill. The PEG coated granules of duloxetine hydrochloride were mixed with microcrystalline cellulose, starch, talc and magnesium stearate. The granules were coated with a seal coat polymer in a fluidized bed processor using Wurster's technique by spraying hypromellose, sucrose and polyethylene glycol 6000 solution in water. The seal coated granules were further coated with enteric polymer suspension prepared by mixing methacrylic acid polymer, sodium hydroxide, talc, triethyl citrate in water in a fluidized bed processor using Wurster's technique. The enteric-coated granules of duloxetine hydrochloride were encapsulated in hard gelatin capsules of a suitable size.

Example 4

TABLE 4

| No | Ingredients | % w/w |
|---|---|---|
| 1 | Duloxetine hydrochloride | 10-80 |
| 2 | Amberlite | 10-80 |
| 3 | Purified water | q.s. |
|   | Seal coating |   |
| 4 | Seal coat composition: (Sucrose, Hypromellose, Polyethylene glycol 6000, Purified water) | 1-30 |
|   | Enteric coating |   |
| 5 | Methacrylic acid copolymer suspension (Methacrylic acid copolymer, sodium hydroxide, Talc, triethyl citrate, purified water) | 5-25 |
|   | Encapsulation |   |
|   | Hard gelatin capsules |   |

Procedure: Duloxetine hydrochloride and amberlite were dispersed in water by continuous mixing resulting in the formation of duloxetine hydrochloride-amberlite conjugate. The conjugate was washed, dried and sized to a suitable size. The duloxetine-amberlite conjugate thus obtained was coated with a seal coat polymer by spraying hypromellose, sucrose and polyethylene glycol 6000 solution in water. The seal coated complex was further coated with enteric polymer suspension prepared by mixing methacrylic acid polymer, sodium hydroxide, talc, triethyl citrate in water. The enteric-coated conjugate of duloxetine hydrochloride-amberlite was encapsulated in hard gelatin capsules of a suitable size.

Example 5

TABLE 5

| No | Ingredients | % w/w |
|---|---|---|
|   | Enteric coated beads of Duloxetine hydrochloride |   |
|   | Inactive core |   |
| 1 | Sugar spheres | 10-90 |
|   | Drug layering |   |
| 2 | Duloxetine hydrochloride | 10-80 |
| 3 | Hypromellose | 5-90 |
| 4 | Polyethylene glycol 6000 | 0.5-10 |
| 5 | Talc | 0.5-10 |
| 6 | Purified water | q.s. |
|   | Seal coating |   |
| 7 | Seal coat composition: (Sucrose, Hypromellose, Polyethylene glycol 6000, Purified water) | 1-30 |
|   | Enteric coating |   |
| 8 | Methacrylic acid copolymer suspension (Methacrylic acid copolymer, sodium hydroxide, Talc, triethyl citrate, purified water) | 5-25 |
|   | Encapsulation in hard gelatin capsules |   |

Procedure: Hypromellose solution was prepared in water and duloxetine hydrochloride along with PEG 6000 was added to hypromellose solution. Talc was dispersed in the above solution using a stirrer. The slurry thus obtained was sprayed on sugar sphere beads in a fluidized bed processor by Wurster technique. The beads of duloxetine or a salt thereof thus obtained were seal coated by spraying hypromellose, sucrose and polyethylene glycol 6000 solution in water. The seal coated beads were further coated with enteric polymer suspension prepared by mixing methacrylic acid polymer, sodium hydroxide, talc, triethyl citrate in water. The enteric-coated beads of duloxetine hydrochloride were encapsulated in hard gelatin capsules of a suitable size.

Example 6

TABLE 6

| No | Ingredients | % w/w |
|---|---|---|
|   | Core minitablets of Duloxetine hydrochloride |   |
| 1 | Duloxetine hydrochloride | 10-80 |
| 2 | Lactose | 10-90 |
| 3 | Starch | 10-90 |
| 4 | Povidone | 1-15 |
| 5 | Isopropyl alcohol | q.s. |
| 6 | Purified water | q.s. |

TABLE 6-continued

| No | Ingredients | % w/w |
|---|---|---|
|  | Core minitablets of Duloxetine hydrochloride |  |
| 7 | Talc | 0.5-10 |
| 8 | Magnesium stearate | 0.5-5 |
| 9 | Colloidal silicon dioxide | 0.5-5 |
|  | Seal coating |  |
| 10 | Seal coat composition: (Sucrose, Hypromellose, Polyethylene glycol 6000, Talc, Purified water) | 1-30 |
|  | Enteric coating |  |
| 11 | Methacrylic acid copolymer suspension (Methacrylic acid copolymer, sodium hydroxide, Talc, triethyl citrate, purified water) | 5-25 |
|  | Encapsulation |  |
|  | Hard gelatin capsules |  |

Procedure: Duloxetine hydrochloride was mixed with lactose, starch and granulated with povidone solution in isopropyl alcohol-water mixture. The granules were dried, mixed with colloidal silicon dioxide and lubricated with magnesium stearate. The lubricated granules were compressed into minitablets of a suitable size using a suitable tooling. The minitablets of duloxetine or a salt thereof were seal coated by spraying hypromellose, sucrose, talc and polyethylene glycol 6000 dispersion in water. The seal coated minitablets were further coated with enteric polymer suspension prepared by mixing methacrylic acid polymer, sodium hydroxide, talc, triethyl citrate in water. The enteric-coated minitablets of duloxetine hydrochloride were encapsulated in hard gelatin capsules of a suitable size.

Example 7

TABLE 7

| No | Ingredients | % Composition |
|---|---|---|
| 1 | Duloxetine hydrochloride | 10-80 |
| 2 | Lactose | 10-90 |
| 3 | Starch | 10-90 |
| 4 | Povidone | 1-15 |
| 5 | Purified water | q.s. |
| 6 | Talc | 0.5-10 |
| 7 | Magnesium stearate | 0.5-5 |
| 8 | Colloidal silicon dioxide | 0.5-5 |
| 9 | Isopropyl alcohol | q.s. |
| 10 | Purified water | q.s. |
|  | Seal coating |  |
| 11 | Seal coat composition: (Sucrose, Hypromellose, Polyethylene glycol 6000, Talc, Purified water) | 1-30 |
|  | Enteric coating |  |
| 12 | Methacrylic acid copolymer suspension (Methacrylic acid copolymer, sodium hydroxide, Talc, triethyl citrate, purified water) | 5-25 |

Procedure: Duloxetine hydrochloride was mixed with lactose, starch and granulated with povidone solution in isopropyl alcohol-water mixture. The granules were dried, and lubricated with magnesium stearate. The lubricated granules were compressed into tablets of a suitable size using a suitable tooling. The duloxetine tablets were seal coated by spraying hypromellose, sucrose, talc and polyethylene glycol 6000 dispersion in water. The seal coated tablets of duloxetine hydrochloride were compressed with talc, magnesium stearate and colloidal silicon dioxide in such a way so that duloxetine tablets were completely covered by other excipients to form a tablet in a tablet dosage form which was further coated with enteric polymer suspension prepared by mixing methacrylic acid polymer, sodium hydroxide, talc, triethyl citrate in water.

While the present invention has been described in terms of its specific embodiments, certain modifications and equivalents will be apparent to those skilled in the art and are intended to be included within the scope of the present invention.

We claim:

1. A solid pharmaceutical composition for oral administration comprising duloxetine resin conjugate, wherein the duloxetine resin conjugate comprising 1% to about 40% by weight of duloxetine or a salt thereof conjugated to ion exchange resin particles to reduce degradation of the duloxetine or pharmaceutically acceptable in acidic pH upon oral administration of the pharmaceutical composition optionally with other pharmaceutically acceptable excipients; wherein the conjugated duloxetine resin particles are coated with pharmaceutically acceptable seal coat polymers followed by enteric coating polymers; wherein the pharmaceutically acceptable enteric polymer comprises one or more of shellac, methacrylic acid copolymer type C NF, cellulose butyrate phthalate, cellulose hydrogen phthalate, cellulose propionate phthalate, hydroxypropyl methylcellulose acetate, dioxypropyl methylcellulose succinate, carboxymethyl ethylcellulose and acrylic acid polymers/copolymers.

2. The composition of claim 1, wherein the ion-exchange resin particles are anionic exchange resin particles.

3. The composition of claim 1, wherein the composition is in the form of granules, pellets, beads, spheroids, a tablet, a minitablet, a microtablet, a capsule, granules in a capsule, pellets in a capsule, microtablets in a capsule and minitablets in a capsule.

4. A process for preparing a pharmaceutical composition comprising duloxetine or a salt thereof conjugated to ion exchange resin particles according to claim 1, the process comprising: a. slurrying anionic exchange resin particles in a solution containing duloxetine to get a resin conjugate; b. washing the duloxetine resin conjugate; c. drying the duloxetine resin conjugate; and d. coating the duloxetine resin conjugate with a pharmaceutically acceptable seal coat polymer followed by an enteric coating polymer.

5. A tablet in a tablet composition of duloxetine or a salt thereof comprising an inner tablet comprising duloxetine or a salt thereof optionally with other pharmaceutically acceptable excipients; and an outer tablet comprising inert pharmaceutically acceptable excipients, wherein the inner tablet of duloxetine or a salt thereof is coated with seal coat polymers followed by enteric coating with one or more pharmaceutically acceptable enteric coat polymer selected from the group consisting of gelatin, shellac, methacrylic acid copolymer type C NF, cellulose butyrate phthalate, cellulose hydrogen phthalate, cellulose propionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose and acrylic acid polymers/copolymers; wherein the pharmaceutically acceptable seal coat polymers comprises one or more of hydroxypropyl methylcellulose, hydroxypropyl cellulose, hydroxyethyl cellulose, hydroxypropyl ethylcellulose, methylcellulose, ethyl cellulose, carboxymethyl cellulose, sodium carboxymethyl cellulose, hydroxyethyl methylcellulose, and mixtures thereof.

6. A process for preparing a tablet in a tablet composition of duloxetine or a salt thereof according to claim 5, the process comprising: a. mixing duloxetine or a salt thereof with pharmaceutically acceptable excipients to form a mixture; b. granulating the mixture with other pharmaceutically acceptable excipients; c. compressing the granules into tablet; d. coating the said tablet with a seal coat polymer; e. compressing the seal coated tablet with other pharmaceutically acceptable excipients and coating the tablet with one or more enteric polymers.

\* \* \* \* \*